United States Patent
Vereecken et al.

(10) Patent No.: US 11,260,361 B2
(45) Date of Patent: Mar. 1, 2022

(54) SYNTHESIS DEVICE

(71) Applicant: IMEC vzw, Leuven (BE)

(72) Inventors: Philippe Vereecken, Liège (BE); Brecht Put, Schulen (BE); Tim Stakenborg, Heverlee (BE); Arnaud Furnemont, Jandrenouille (BE); Luca Di Piazza, Wezembeek-Oppem (BE)

(73) Assignee: IMEC VZW, Leuven (BE)

( * ) Notice: Subject to any disclaimer, the term of this patent is extended or adjusted under 35 U.S.C. 154(b) by 218 days.

(21) Appl. No.: 16/411,811

(22) Filed: May 14, 2019

(65) Prior Publication Data

US 2019/0355964 A1 Nov. 21, 2019

(30) Foreign Application Priority Data

May 17, 2018 (EP) ..................................... 18172921

(51) Int. Cl.
  *B01J 19/00* (2006.01)
  *C25B 3/29* (2021.01)
  (Continued)

(52) U.S. Cl.
  CPC ........ *B01J 19/0046* (2013.01); *C01G 23/047* (2013.01); *C07H 21/00* (2013.01);
  (Continued)

(58) Field of Classification Search
  CPC .................................................. B01J 19/0046
  See application file for complete search history.

(56) References Cited

U.S. PATENT DOCUMENTS 9,394,167 B2 * 7/2016 Maurer .................... C25B 9/17
2002/0008038 A1 1/2002 Heller et al.
(Continued)

FOREIGN PATENT DOCUMENTS

EP 3569306 B1 * 11/2020 .......... B01J 19/0046

OTHER PUBLICATIONS

Li et al, Both Cationic and Anionic Co-(de)intercalation into a Metal-Oxide Material, Joule, vol. 2, Issue 6, Jun. 2018, pp. 1134-1145 (Year: 2018).*

(Continued)

*Primary Examiner* — Harry D Wilkins, III
(74) *Attorney, Agent, or Firm* — Knobbe, Martens, Olson & Bear, LLP

(57) ABSTRACT

A device for synthesis of macromolecules is disclosed. In one aspect, the device comprises an ion-releaser having a synthesis surface comprising an array of synthesis locations arranged for synthesis of the macromolecules. The ion-releaser also includes an ion-source electrode, which is arranged to contain releasable ions and is arranged to be in contact with each of the synthesis locations of the synthesis surface, thereby release ions to the synthesis locations. The ion-releaser further comprises activating electrodes, which are arranged to be in contact with the ion-source electrode, wherein each one of the activating electrodes is arranged in association with one of the synthesis locations via the ion-source electrode. The ion-releaser is arranged to release at least a portion of the releasable ions from the ion-source electrode to one of the synthesis locations, by activation of the activating electrode associated with the synthesis location.

19 Claims, 2 Drawing Sheets

(51) Int. Cl.
| | |
|---|---|
| *C25B 9/19* | (2021.01) |
| *C25B 9/70* | (2021.01) |
| *C01G 23/047* | (2006.01) |
| *C07H 21/00* | (2006.01) |
| *H01B 1/12* | (2006.01) |

(52) U.S. Cl.
CPC ............... *C25B 3/29* (2021.01); *C25B 9/19* (2021.01); *C25B 9/70* (2021.01); *H01B 1/122* (2013.01); *B01J 2219/00713* (2013.01)

(56) References Cited

U.S. PATENT DOCUMENTS

| | | | |
|---|---|---|---|
| 2003/0077642 A1* | 4/2003 | Fritsch ................. | B01J 19/0046 435/6.12 |
| 2003/0190632 A1 | 10/2003 | Sosnowski et al. | |
| 2004/0048241 A1* | 3/2004 | Freeman ............ | G01N 33/5438 435/5 |

OTHER PUBLICATIONS

Extended European Search Report issued in European Patent Application No. 18172921.1, dated Sep. 7, 2018.

* cited by examiner

SYNTHESIS DEVICE

CROSS-REFERENCE TO RELATED APPLICATIONS

This application claims foreign priority to European Application EP 18172921.1, filed on May 17, 2018, which is incorporated herein by reference in its entirety.

BACKGROUND

Technological Field

The disclosed technology relates to a device for synthesis of macromolecules. The disclosed technology further relates to a method of synthesis of macromolecules using the synthesis device.

Description of the Related Technology

In the chemical synthesis of molecules and macromolecules such as DNA and RNA, the presence of ions may be desired or necessary. For example, ions may induce or catalyze a reaction step. For example, in synthesis of biomacromolecules, such as nucleic acids or saccharides, protection of hydroxyl groups is often a necessary step. Different acid-labile protective groups are known to be used for this purpose and a suitable deprotection method is needed to obtain desired end products. One example is the detritylation of nucleic acid hydroxyl groups in oligonucleotide synthesis. The protective group may for this and other examples be removed in acidic media thus preparing the molecule for further reaction, such as reaction with a nucleotide during oligonucleotide synthesis. Molecular synthesis may be performed in a synthesis array comprising an array of synthesis locations. Such synthesis arrays may find use in data storage applications using molecular memory, a field of growing interest fueled by increasing amounts of generated data.

In synthesis arrays or micro synthesis arrays, local generation of ions is desired for local control of the chemical reaction or site selective synthesis in specific synthesis locations. Local control in synthesis array applications may be achieved via appropriate electrochemical reactions that produce protons, or H+, using patterned platinum electrode arrays and a suitable redox active agent whereby protons are released by either electrochemical oxidation or reduction at the platinum electrodes. Thereby, electrochemical reaction may induce protons on one or more of the electrodes in the array. However, it is a problem that the electrochemically generated acid diffuses away from the electrolyte to neighboring electrodes, thus requiring, for example, neutralizing bases, or proton consuming counter reactions. Another disadvantage is that a redox active electrolyte may be needed for such acid production, which may interfere with the synthesis and synthesis products.

Thus, there is a need for devices and methods for synthesis of macromolecules in arrays, which allow for efficient provision of ions needed for the synthesis, while providing local control of the provision in the array.

SUMMARY OF CERTAIN INVENTIVE ASPECTS

It would be desirable to allow release of ions, and control thereof, to synthesis locations in an array of synthesis locations such that the release of ions to the synthesis locations may be selectively and individually controlled, without disadvantages of prior art.

An objective of the disclosed technology is to address this issue. A further objective is to provide solutions to problems related to prior art. Further and alternative objectives may be understood from the following.

A first aspect of the disclosed technology relates to a device for synthesis of macromolecules. The device comprises an ion-releaser having a synthesis surface comprising an array of synthesis locations arranged for synthesis of the macromolecules, wherein the ion-releaser comprising an ion-source electrode arranged to comprise releasable ions, and arranged to be in contact with each of the synthesis locations of the synthesis surface, thereby arranged to release ions to the synthesis locations, and activating electrodes arranged to be in contact with the ion-source electrode, wherein each one of the activating electrodes is arranged in association with one of the synthesis locations, respectively, via the ion-source electrode, and wherein the ion-releaser is arranged to release at least a portion of the releasable ions from the ion-source electrode to one of the synthesis locations, by activation of the activating electrode associated with the one of the synthesis locations.

The first aspect of the disclosed technology is based on the insight that associating or connecting an activation electrode to each synthesis location and in contact with an ion-source electrode enables individual control of release of ions to each synthesis location. Thus, by enabling control of release of ions to the synthesis locations, control of synthesis of macromolecules in connection with each synthesis location is enabled. Control of release of ions may enable control of, for example, initiating, halting, accelerating, or decelerating of the synthesis. The ions may function, for example, to adjust pH, such as if released ions are protons, or hydroxyl ions, thereby having an effect on synthesis, for example, by catalyzing the synthesis. Released ions may further have other effects on synthesis reactions, such as catalytic effects other than pH-related or be directly or indirectly involved in synthesis reactions.

The ion-releaser having a synthesis surface comprising an array of synthesis locations arranged for synthesis of the macromolecules, provides for efficient synthesis of macromolecules in different locations, and enables addressing of a plurality of locations for macromolecule synthesis.

The ion-releaser comprising an ion-source electrode arranged to comprise releasable ions, and arranged to be in contact with each of the synthesis locations of the synthesis surface, enables controlled release of ions to the synthesis locations.

The synthesis surface or synthesis locations may comprise a porous oxide onto which the synthesis of the macromolecule may take place. The porous oxide may be for introducing OH-groups, i.e. making OH-groups available for the synthesis reaction. This may be advantageous in that it facilitates DNA synthesis independent of the ion-source electrode. Thus, to promote selective synthesis at the synthesis locations, the synthesis locations may be covered by a porous membrane such as porous silica or a solid electrolyte material, or a combination thereof. Alternatively, the ion-source material may be embedded in a nanoporous dielectric thereby forming different synthesis locations; for example, titania/silica nanoporous electrodes may be used for intercalation of many ions such as $H^+$, $Li^+$, $Al^{3+}$ and $Na^+$.

Alternatively, the ion source electrode may be covered by a solid electrolyte. The solid electrolyte may form a dense layer through which ions may diffuse from the ion source to the synthesis location in contact with synthesizing medium and vice versa when the ion-source electrode is "loaded" again with ions. The role of the solid electrolyte may further be protective; i.e. to prevent corrosion or dissolution of the ion-source material in the synthesis medium or solution.

The activating electrodes arranged to be in contact with the ion-source electrode, wherein each one of the activating electrodes is arranged in association with one of the synthesis locations, respectively, via the ion-source electrode, enables release of ions from the ion-source electrode to one, or more, of the synthesis locations. The ion-releaser being arranged to release at least a portion of the releasable ions from the ion-source electrode to one of the synthesis locations, by activation of the activating electrode associated with the one of the synthesis locations, allows for controlling of the ion release to one or more of the synthesis locations.

The device, and methods taking advantage of the device, benefits from that ions may be released directly into solution in contact with the synthesis locations(s), where an effect of the ions is desired, without a need for addition of, for example, a redox active material for proton generation. A further advantage of the device is that many ions can be introduced, thus enabling a large range of reactions, for example, catalytic reactions. For example, $H^+$, $Li^+$, $Na^+$, $K^+$, $Ca^{2+}$, $Cu^+$ or $Mg^{2+}$, or combinations thereof, may be released.

The synthesis may be synthesis of macromolecules, for example, on patterned substrates. The macromolecules may be, provided as examples but not limited to, DNA, RNA or proteins, and modifications and analogues thereof. The disclosed technology enables local, such as in synthesis locations, generation of ions providing effect on the synthesis of the macromolecules. As non-limiting example, the ions may be protons or hydroxyl anions providing catalytic effects on the synthesis reaction, for example, of a pH-sensitive reaction.

The aspects of the disclosed technology may be used for memory writing or storing purposes, for example, writing data in the form of bits on a type of DNA or RNA, or other suitable macromolecules. The synthesis device may be part of a molecular memory.

The ion-source electrode may be an insertion electrode. An insertion electrode may be capable of having ions reversibly inserted in the electrode. The insertion electrode may be an intercalation type electrode, a conversion type electrode or an alloying type electrode.

In some embodiments, the ion source electrode is an ion intercalation electrode.

Such electrodes may efficiently store and release the ions. Furthermore, such electrodes may be recharged with ions.

The ion intercalation electrode may comprise a material selected from amorphous $TiO_2$, amorphous chlorine doped $TiO_2$, nanoporous titania/silica composites, $WO_3$, NiO, $Ti_2Ni$, $Ni(OH)_2$ and different Li-electrodes. Such a material may be used to store and release ions, for example, ions selected from the group consisting of $H^+$, $Li^+$, $Na^+$, $K^+$, $Ca^{2+}$, $Mg^{2+}$, $Al^{3+}$, $OH^-$, $Cl^-$, $F^-$ and combinations thereof. Furthermore, it may be recharged with ions when fully or partly depleted of ions.

Furthermore, the intercalation electrode may be provided with the ions inserted or released into the host material by solid-state diffusion upon oxidation (typically with release of cation but intercalation of anion is also possible) and reduction (typically intercalation of cation but release of anion is also possible) of, e.g., a host transition metal such as Co(IV,III), Ni (IV,III), Mn(IV,III), Ti (IV,III), V(IV,III). The intercalation materials may be layered structures such as graphite and metal dichalcogenides (e.g. $TiS_2$, $WS_2$) or oxides such as $MNO_2$ ($M=Li^+$, $Na^+$, $K^+$ and N=combinations of Co, Ni, Mn and Al). Furthermore, olivine ($LiMPO_4$) with M=Fe, Co, Mn and Ti and spinel structures (e.g. $LiMn_2O_4$) are useful as intercalation materials. Protons may also intercalate in materials such as $TiO_2$, $WO_3$, NiO, $V_2O_5$ and even graphite, and the intercalation electrode may thus comprise such materials.

A conversion type electrode may be arranged to involve a chemical change in the material with release of the ions; this type of electrode may be useful for anions such as hydroxides.

An alloying type electrode may be suitable for hydrogen storage. The alloy may comprise metal hydrides, such as metal hydrides of Pt and/or Pd.

The ion source electrode material may comprise a material selected from $LaNi_5$, LaMgNi, TiFe, $Mg_2Ni$, $TiO_2$, $TiSi_2$, $ZrV_2$, $ZrMn_2$, $TiMn_2$, $CeNi_3$, $YFe_3$, $Y_6Fe_{23}$, ZrNi, $Ti_2Ni$, $MnO_2$, $WO_3$ and $Ni(OH)_2$.

Furthermore, the ion source electrode material may be selected from $BaZrO_3$, $BaTbO_3$ and $SrTiO_3$.

The ion source electrode may be arranged so that it is in contact with a plurality of synthesis locations. Thus, the ion-source electrode may comprise a full or partial plate of underneath the synthesis locations. Thus, the device may comprise a single ion-source electrode under the synthesis locations.

In this case the activating electrodes may be positioned under the openings and the voltage and current applied may be such that the ion release is confined only to the synthesis locations.

Furthermore, if the ion release electrode materials of the ion source electrode are oxides or semiconductor with high electronic resistance, the spreading resistance in the material may be such that the activating electrodes will activate only the ion-source material under the synthesis location. An advantage of such design, i.e. having a single full or partial plate of underneath all synthesis locations, is that a much larger capacity of ions is foreseen compared to having a plurality of different ion-source materials positioned under the cavity or its proximity. Another advantage is that the ions in the ion-release electrode under the cavity may be replenished as soon as the activating electrode under this synthesis location is switched off. This happens because the whole plate may seek its new equilibrium moving ions from neighboring locations until the ion concentration is the same everywhere again.

The distance between the synthesis locations and the thickness of the ion release electrodes may be designed such that the sheet resistance of the layer is high enough to avoid interference with neighboring synthesis locations and confine release of ions at the synthesis location above the activating electrode only.

In some embodiments, the synthesis device may comprise a plurality of ion-source electrodes, wherein each one of the plurality of the ion-source electrode is arranged in connection with one of the synthesis locations, respectively.

This embodiment may be used if the conductivity of the ion source electrode is too high to place the synthesis locations close-enough together with sufficient ion-release electrode thickness. Thus, the ion-source electrode may be arranged as a plurality of electrically isolated pads (of any shape) located mostly under the synthesis locations. In this case, it may be possible to maximize the available area under and in-between synthesis locations to maximize the capacity of ions. In this case the thickness of the ion-source electrode may be adjusted to assure that sufficient ion capacity is available for the desired synthesis.

The synthesis locations may be arranged to be in contact with reactants, reaction products, and reaction medium, thereby facilitating synthesis at or adjacent to the synthesis locations.

The activating electrodes may be of metal current collector type or transistor type.

The synthesis device may further comprise a counter electrode at a distance from the synthesis surface, wherein activation of the activating electrode associated with the one of the synthesis locations is realized by provision of voltage and/or current between the activating electrode and the counter electrode. Thereby, one way of activating the activating electrodes may be realized.

Such an external counter electrode may be placed anywhere near the activating electrode.

In some embodiments, the counter electrode may be arranged opposing the synthesis surface, or facing the synthesis surface, a distance away from the synthesis surface. Thus, the counter electrode may be arranged such that the ion source electrode is arranged between the activating electrode and the counter electrode. Thereby, a distance may be provided between the activating electrode and the counter electrode. The counter electrode, which may be of insertion electrode type, may thus be arranged as a "thief" electrode, for absorbing or collecting released ions.

The synthesis device may further comprise a control unit arranged to control activation of the activating electrodes. Furthermore, individual activation of each one of the activating electrodes may be realized. Thus, synthesis may be controlled, and controlling of synthesis in desired or selected synthesis locations are realized.

The synthesis device may further comprise:
a synthesis plate comprising a first side and a second side and an array of through holes, one for each of the synthesis locations, the through holes extending from the first side to the second side of the synthesis plate, wherein
the first side of the synthesis plate is arranged to be in contact with the synthesis surface of the ion-releaser, such that each of the through holes is associated with one of the synthesis locations, respectively, wherein the synthesis surface of the ion-releaser forms a bottom portion of each of the through holes, thereby defining a synthesis cavity in each of the through holes comprising a synthesis location.

The second side of the synthesis plate may thus be opposing or opposite the first side of the synthesis plate. Thus, the second side and the first side may have normal vectors pointing in two different and substantially parallel directions. As discussed above, the synthesis surface or synthesis locations may comprise a porous oxide onto which the synthesis of the macromolecule may take place. Thus, if the synthesis locations are located in cavities, only the bottom of the cavity may comprise a porous oxide in order to provide attachment of the macromolecule to the bottom instead of the sidewalls.

For many synthesis reactions, —OH terminated surfaces may be needed. If silica is used as synthesis plate, the synthesis may start on the silica side wall rather than on the bottom of the cavity where the synthesis location and ion source electrode; e.g., $TiO_2$, $MnO_2$, vanadium oxide are located. To reduce this risk, the sidewalls of the cavities may be coated with another dielectric such as silicon nitride. However, the bottom of the cavities may be covered by, for example, a porous silica with high OH termination, thus attachment of the synthesized molecule to this porous oxide as substrate is more likely.

The synthesis plate further adds to reducing a risk of ions undesirably entering adjacent synthesis locations. Furthermore, any undesired mass transport between synthesis locations may be reduced or avoided.

As discussed above, a counter electrode may be positioned such that a voltage and/or current between the activating electrode and the counter electrode it is capable of activating the activating electrode. As an example, the counter electrode may be arranged at the other side of the synthesis plate than the ion source electrode. The counter electrode may be arranged opposing the second side of the synthesis plate. Thereby, the counter electrode may efficiently be arranged as a "thief" electrode, for absorbing or collecting released ions, thus preventing them from leaving a synthesis cavity. For such a purpose, the counter electrode may be of insertion electrode type.

The counter electrode may be arranged to be in contact with the second side of the synthesis plate. The counter electrode may further comprise openings in connection with each synthesis cavity, thereby allowing transport of matter into or out of each synthesis cavity.

Such a positioned counter electrode may efficiently realize movement of the releasable ions into a synthesis cavity associated with the synthesis location. The positioning of the counter electrode reduces or avoids undesired risks of released ions entering neighboring synthesis locations, when the counter electrode is of insertion electrode type. The counter electrode may thus be a "top-thief" electrode. When the counter electrode is arranged to be in contact with the second side of the synthesis plate, a thin-film conductor may be placed underneath, i.e. between the counter electrode and the second side of the synthesis plate. Thus, a thin film conductor layer may be provided between the synthesis plate and the counter electrode to allow better contacting of the counter electrode. As an alternative, the thin film may be provided on top of the counter electrode, i.e. arranged to be in contact with the synthesizing liquid. The thin-film conductor may comprise TiN or any inert conductive metal or alloy.

The counter electrode may be of a film type.

Furthermore, the counter electrode may be an ion source electrode, which may be capable of capture or absorbing ions. This may thus be the reverse of the release step at the ion source electrode. The counter electrode may be an insertion electrode such as an intercalation electrode. Having an insertion electrode as counter electrode on-top of the second side of the synthesis plate is advantageous in that it decreases the risk of ions escaping the synthesis cavities and diffusing to neighboring cavities. The counter electrode may be of the same type of insertion electrode as the ion source electrode. Thereby, a voltage difference needed for release of the ions may be small.

The synthesis plate may be made of a dielectric material.

The releasable ions may be ions acting as reactants in the synthesis of the macromolecules, or providing catalytic effects on the synthesis of the macromolecules.

The releasable ions may be selected from $H^+$, $Li^+$, $Na^+$, $K^+$, $Al^{3+}$, $Ca^{2+}$, $Cu^+$ and $Mg^{2+}$, and combinations thereof.

The counter electrode may comprise or be made of a material arranged to capture or absorb the ions. Thereby, the ions may be confined to the adjacency of the synthesis location to which the ions were released, such as the synthesis cavity of the synthesis location. Thus, pH-changes or other synthesis parameters provided by the ions, may be confined to desired synthesis location(s).

The counter electrode and the ion-source electrode may be made of same material.

By use of a same material for the ion-source electrode and the counter electrode, the voltage needed to activate the electrodes may be small, for example, less than a few hundred millivolts, which enables use of small sizes of the activating electrode.

The device may be further arranged for comprising a synthesis liquid in contact with one or more of the synthesis locations. The synthesis liquid may be an aqueous liquid, such as essentially consisting of water, and may comprise additives, ions, buffering agents, reagents and other suitable chemicals or compounds.

The synthesis liquid may further be a non-aqueous liquid, such as a solvent selected from acetonitrile, carbonates, methanol, ethanol, and dimethylformamide (DMF). An example of a non-aqueous solution that can provide protons is methane sulfonic acid in propylene carbonate. In this case, the protons can be inserted into $TiO_2$ upon reduction of Ti(IV) to Ti(III) and released again upon the oxidation of Ti(III) to Ti(IV).

The synthesis liquid can be an ionic liquid and mixtures of ionic liquid and salts.

A second aspect of the disclosed technology relates to a method of synthesis of macromolecules using a synthesis device according to the first aspect, wherein the macromolecules are synthesized on at least one of the synthesis locations, the method comprising: providing reactants for the synthesis on at least one of the synthesis locations; releasing at least a portion of the releasable ions from the ion-source electrode to the at least one of the synthesis locations; and synthesizing the macromolecules from the reactants in the presence of the released ions, on the at least one of the synthesis locations.

The released ions may provide catalytic effects, and/or have an effect on pH, and/or act a reagent or reactant, for the synthesis. The released ions may be contacted with the macromolecule.

BRIEF DESCRIPTION OF THE DRAWINGS

The above, as well as additional objectives, features and advantages of the disclosed technology, will be better understood through the following illustrative and non-limiting detailed description, with reference to the appended drawings. In the drawings like reference numerals will be used for like elements unless stated otherwise.

DETAILED DESCRIPTION OF CERTAIN ILLUSTRATIVE EMBODIMENTS

Figure 1A:
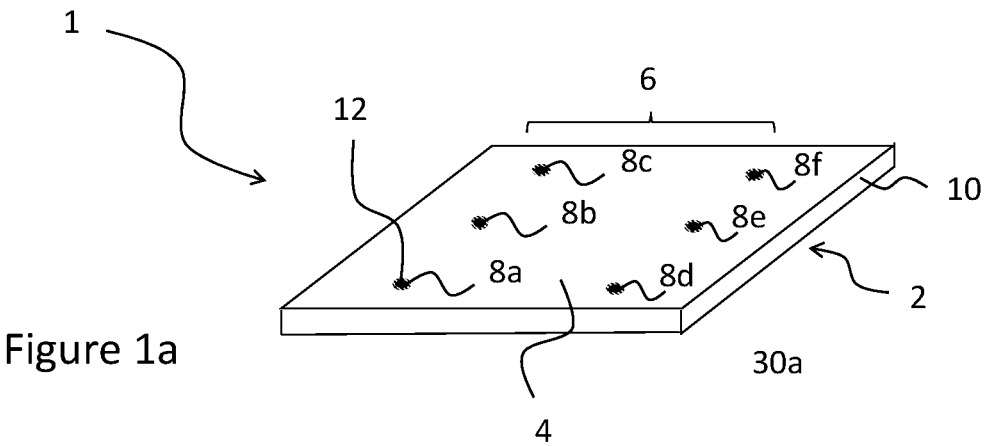
FIG. 1A is a schematic perspective view of a synthesis device.
Figure 1B:
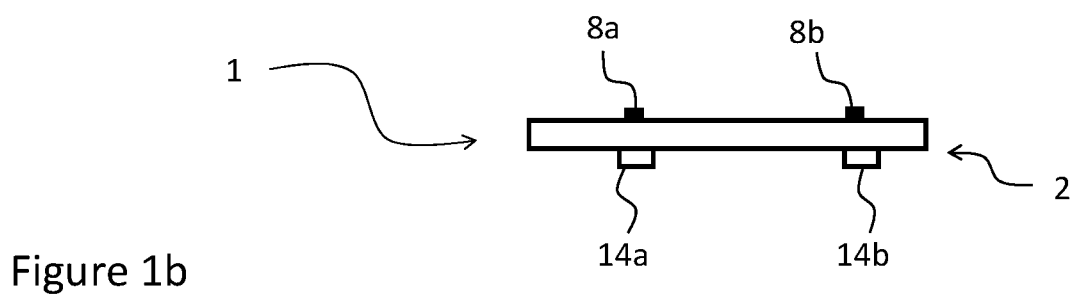
FIG. 1B is a schematic side view of the synthesis device of FIG. 1A.

With reference to FIGS. 1A and 1B, a synthesis device 1 for synthesis of macromolecules will now be discussed. The device 1 comprises an ion-releaser 2 having a synthesis surface 4 comprising an array 6 of synthesis locations 8a-f arranged for synthesis of the macromolecules (not illustrated). The ion-releaser 2 comprises an ion-source electrode 10 arranged to comprise releasable ions (not illustrated), and arranged to be in contact 12 with each of the synthesis locations 8a-f of the synthesis surface 4, thereby arranged to release ions to the synthesis locations 8a-f, and activating electrodes 14a, (in this illustrated example six activating electrodes are provided of which two are visualised in FIG. 1B, and of which none are visible in FIG. 1A) arranged to be in contact with the ion-source electrode 10, wherein each one of the activating electrodes 14a,b is arranged in association with one of the synthesis locations 8a-f, respectively, via the ion-source electrode 10, and wherein the ion-releaser 2 is arranged to release at least a portion of the releasable ions from the ion-source electrode 10 to one of the synthesis locations 8a-d, by activation of the activating electrode 14a,d associated with the one of the synthesis locations. For the sake of clarifying the example and with further reference to FIG. 1B, it may be that activating electrode 14a is activated and associated with synthesis location 8a. The ion-source electrode may be an ion intercalation electrode, which may comprise a material selected from, but not limited to, amorphous $TiO_2$, amorphous chlorine doped $TiO_2$, and nanoporous titania-silica composite.

The synthesis surface 4 may be a porous oxide, a solid electrolyte or combinations thereof.

The synthesis locations are disclosed as comprised by the synthesis surface. It will be understood, at least in part from the examples and as discussed herein below, that the synthesis locations in this meaning may be portions or part of the synthesis surface of the ion-source electrode.

Although the synthesis device 1, as illustrated in FIG. 1, may comprise a single ion-source electrode 10, the synthesis device may comprise a plurality of ion-source electrodes 10, wherein each one of the plurality of the ion-source electrodes 10 may be arranged in connection with one of the synthesis locations 8a-f, respectively.

With further reference to FIG. 1, it shall be understood from the discussions herein that the synthesis device suitably may be used for synthesis of macromolecules in solution. For such a synthesis, the synthesis locations 8a-f may be contacted with synthesis medium, such as an aqueous liquid, non-aqueous or mixed liquid comprising suitable compounds such as selected from reagents, buffering agents, and salts. This may be realized, for example, by providing the synthesis medium in contact with the synthesis locations 8a-f, or at least a portion of the synthesis surface 4 comprising at least a portion of the array 6 of the synthesis locations 8a-f may be provided with the synthesis medium. The macromolecule being synthesized on a synthesis location 8a-f may be linked to the synthesis location 8a-f, such as by being linked to the ion-source electrode contacted therewith. The material of the ion-source electrode 10 according to some embodiments may efficiently be used for such binding.

The synthesis device 1 may further comprise a counter electrode (not shown in FIG. 1). This may be used for activating the activating electrodes 14a,b. The counter electrode may have a large area, such as an area larger than the ion source electrode 10. The counter electrode may be of any suitable material, such as an inert material or alloy, e.g. Pt or stainless steel.

Furthermore, the synthesis device 1 may comprise a third electrode, such as a reference electrode (not shown in FIG. 1). The reference electrode may have a controlled and mostly constant electrode potential which may be used for monitoring and controlling the ion-release electrodes.

For synthesis of, for example, DNA or RNA, the macromolecule may be linked to the synthesis location 8a-f, such as by a formed bond or interaction with the material of the synthesis location.

It shall be appreciated that the number of synthesis locations may be larger than what is illustrated by the schematic illustrations. The number of synthesis locations on a synthesis device may be from a few, such as three, and up to hundreds, up to thousands, or up to millions, or even above millions.

It shall be understood that, for example, DNA or RNA synthesis may be performed on a device discussed with reference to FIGS. 1A and 1B, and with reference to the other figures. For the sake of such an example and with reference to FIGS. 1A and 1B, it may now be assumed that at a given time it is desired to synthesize DNA in synthesis locations 8 a and e. The chemistry for the example is selected such that DNA synthesis requires removal of protecting groups, which is realized by lowering pH, or increasing concentration of protons. The synthesis takes place in a liquid medium provided at the synthesis locations 8*a-f* comprising necessary compounds for the synthesis. The compounds may be provided by suitable microfluidic means and methods. By activating electrodes 14 *a* and *e*, associated with synthesis locations 8 *a* and *e*, respectively, the ion-source electrode 10, being charged with protons, releases protons to synthesis locations 8 *a* and *e*, where the protons act in lowering pH and thereby act in removal of protection groups, thus allowing synthesis of DNA to proceed. If desired, the pH may be increased or regained, for example, by flushing with buffering solutions.

RNA and DNA synthesis using the synthesis device 1 may be performed by introducing template or precursor solution, i.e. a synthesizing liquid, comprising nucleotides of a specific type (e.g. nucleotides comprising cytosine "C"), allowing them to react at specific array positions (such as 8*a* and *f*), then another precursor solution comprising nucleotides of a second type (e.g. nucleotides comprising guanine "G") is introduced over the synthesis surface 4. These are allowed to react at other positions, such as 8*a*, 8*c* and 8*f*, etc. Thus, the whole synthesis surface 4 may be in contact with the precursor medium, and the electrodes at the synthesis locations provide the selectivity.

The solution may be flushed at times using pumps and microfluidics.

It shall be realized that the device and method may be used for synthesis of other types of molecules, by releasing protons or other ions necessary or desired for the synthesis.

Figure 2:
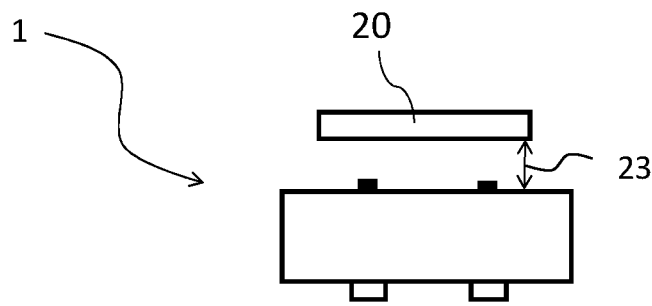
FIG. 2 is a schematic side view of synthesis device comprising a counter electrode.

FIG. 2 illustrates a synthesis device similar to the device discussed with reference to FIG. 1, with the difference that the device of FIG. 2 further comprises a counter electrode 20 arranged opposing the synthesis surface 4 at a distance 23 from the synthesis surface 4. Activation of the activating electrode 14*a-f* associated with the one of the synthesis locations 8*a-f* is realized by provision (not illustrated) of voltage and/or current between the activating electrode 14*a-f* and the counter electrode 20. A control unit (not illustrated) may be arranged to control activation of the activating electrodes 14*a-f*.

In the embodiments discussed in relation to FIGS. 1 and 2, the synthesis device is realized as an electrochemical cell with macroscopic counter electrode and optionally reference electrode.

In another embodiment, an array of synthesis cavities is introduced as electrochemical cell with built-in counter electrode. This may be advantageous in that it allows for smaller distances between the synthesis locations since the risk of contamination between spots is decreased if the synthesis locations are provided within cavities. Such an embodiment is further discussed in relation to FIG. 3 below.

Figure 3:
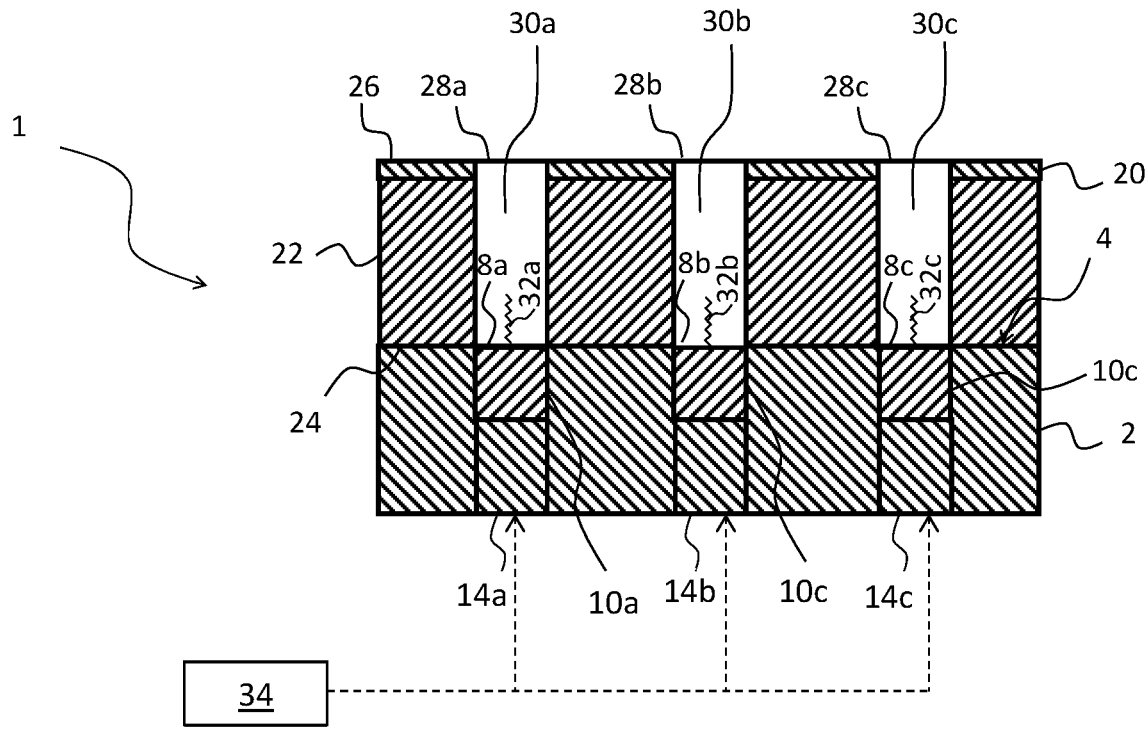
FIG. 3 is a schematic cutaway view of a synthesis device.

With reference to FIG. 3, a synthesis device 1 will now be further described by schematic illustrations. The synthesis device of FIG. 3 is schematically illustrated as a "cut-out" side view, which illustrates three synthesis locations 8*a-c* of an array of synthesis locations. The synthesis device 1 comprises an ion-releaser 2 having a synthesis surface 4 comprising the synthesis locations 8*a-c* arranged for synthesis of the macromolecules. The synthesis locations are thus on the exposed surface of the synthesis surface, i.e. a surface that is not covered by the synthesis plate 22. The ion-releaser 2 comprises a plurality of ion-source electrodes 10*a-c*, in this example being of ion intercalation electrode type or conversion type charged with releasable protons, wherein each one of the plurality of the ion-source electrode 10*a-c* is arranged in association with the synthesis locations 8*a-c* as illustrated in FIG. 3, thereby the ion-source electrodes being arranged to release ions to the synthesis locations 8*a-c*.

In another embodiment, a single ion-source electrode may be used, for example, of a thin layer or thin film type. In another embodiment, a pattern of ion-source electrodes is used whereby each ion-source electrode is contacted to multiple synthesis locations. In yet another embodiment, the patterned can consist of different types of ion-source electrodes; for example, one type for protons or $H^+$ cations and another type for hydroxyl or $OH^-$ anions.

Further illustrated is activating electrodes 14*a-c* arranged to be in contact with the ion-source electrodes 10*a-c*, wherein each one of the activating electrodes 14*a-c* is arranged in association with one of the synthesis locations 8*a-c*, respectively, via the ion-source electrodes 14*a-c*. The ion-releaser 2 is arranged to release at least a portion of the releasable ions from the ion-source electrodes 10*a-c* to one of the synthesis locations 8*a-c*, by activation of the activating electrode 14*a-c* associated with the one of the synthesis locations 8*a-c*. In the illustrated example, activating electrode 14*a* is associated with synthesis location 8*a* via ion-source electrode 10*a*. The synthesis device further comprises a synthesis plate 22 comprising a first side 24 and an opposing second side 26 and an array of through holes 28*a-c*, one for each of the synthesis locations 8*a-c*, the through holes 28*a-c* extending from the first side 24 to the second side 26 of the synthesis plate 22.

The first side 24 of the synthesis plate 22 is arranged to be in contact with the synthesis surface 4 of the ion-releaser 2, such that each of the through holes 28*a-c* is associated with one of the synthesis locations 8*a-c*, respectively, wherein the synthesis surface 4 of the ion-releaser 2 forms a bottom portion of each of the through holes 28*a-c*, thereby defining a synthesis cavity 30*a-c* in each of the through holes 28*a-c* comprising a synthesis location 8*a-c*.

The synthesis surface may have an additional layer of porous membrane, e.g. porous silica or an electrolyte.

The counter electrode 20 is arranged opposing the second side 26 of the synthesis plate 22. The counter electrode 20 is, in this embodiment, arranged to be in contact with the second side of the synthesis plate, wherein the counter electrode comprises openings in connection with each synthesis cavity, thereby allowing transport of matter into or out of each synthesis cavity, as illustrated in FIG. 3. The counter electrode, when being of insertion electrode type and possibly further being made of the same material as the ion source electrode material, thus may function as a "top-thief electrode". In other words, the counter electrode 20 prevents ions to be exiting the cavity as they are taken by the counter electrode in a reverse ion insertion (e.g. intercalation or conversion) reaction. Therefore, it is possible that "symmetric" electrodes are used in the electrochemical cell that is formed over the cavity. In the case of symmetric electrodes, the electrodes or of the same type and material, where one is used to release ions (e.g. anode in case of cation release and cathode in the case of anion release) and the other takes up ions (e.g. cathode in the case of cation uptake and anode in the case of anion uptake).

Further advantages with the counter electrode being of insertion electrode type includes that the ion source electrode may be recharged by releasing the ions from the counter electrode and absorbing them in the ion source electrodes, thereby recharging the ion source electrode.

The synthesis plate 22 may be made of a dielectric material. For sufficient electrical contact to the counter electrode material, it is possible that a thin conductor layer or film is provided between the dielectric synthesis plate 22 and the counter electrode 20.

As an alternative, the synthesis plate 22 may be made on a solid electrolyte material, where the ion source electrode and the counter electrode are ionically connected.

In synthesis cavities 30a-c, macromolecules 32a-c are schematically illustrated linked to the bottom portion of the synthesis cavities 30a-c. For example, the macromolecules may be DNA being synthesized, wherein protecting groups are removed under influence of protons being released into synthesis cavities 30a-c. The control of which synthesis cavities shall receive ions, and thereby control of synthesis, may be realized by a control unit 34. The control unit 34 is suitably linked or connected to the activating electrodes 14a-c and counter electrode 26, which is schematically illustrated by dotted lines in FIG. 3.

Figure 4:
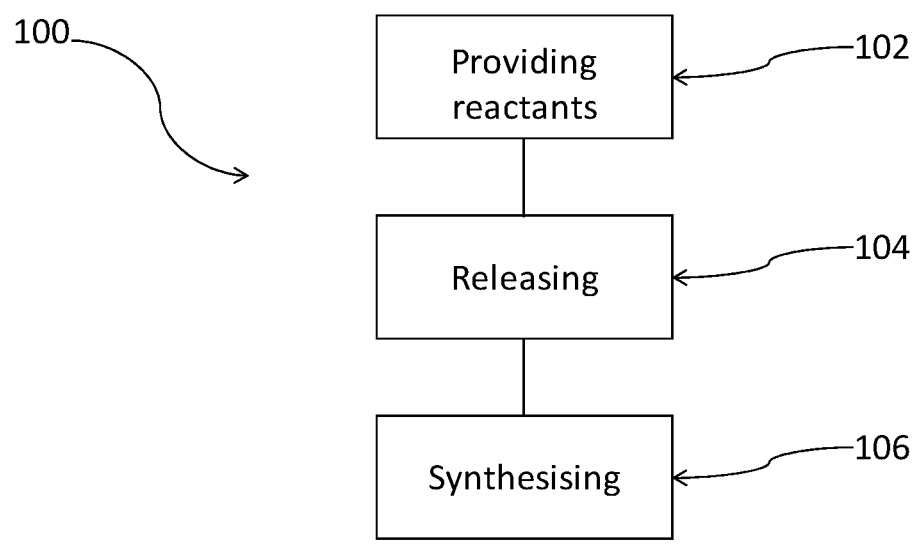
FIG. 4 schematically illustrates a method of synthesis of macromolecules.

FIG. 4 schematically illustrates a method 100 for synthesis of macromolecules using a synthesis device 1 according to the first aspect, wherein the macromolecules are synthesized on at least one of the synthesis locations 8a-f. The method 1 comprises:

providing reactants 102 for the synthesis on at least one of the synthesis locations 8a-f, releasing 104 at least a portion of the releasable ions from the ion-source electrode 10 to the at least one of the synthesis locations 8a-f, and synthesizing 106 the macromolecules from the reactants in the presence of the released ions, on the at least one of the synthesis locations.

The method may further comprise the step of repeating all or any one of the steps above so as to grow a macromolecule such as DNA base pair by base pair.

In the above, the inventive concept has mainly been described with reference to a limited number of examples. However, as is readily appreciated by a person skilled in the art, other examples than the ones disclosed above are equally possible within the scope of the inventive concept, as defined by the appended claims.

What is claimed is:

1. A device for synthesis of macromolecules, the device comprising:
   an ion-releaser having a synthesis surface comprising an array of synthesis locations arranged for synthesis of the macromolecules, wherein
   the ion-releaser comprises:
      an ion-source electrode being an ion intercalation electrode and thereby arranged to comprise releasable ions, and arranged to be in contact with each of the synthesis locations of the synthesis surface, thereby releasing ions to the synthesis locations; and
      activating electrodes arranged to be in contact with the ion-source electrode, wherein each one of the activating electrodes is arranged in association with one of the synthesis locations, respectively, via the ion-source electrode,
   wherein the ion-releaser is arranged to release at least a portion of the releasable ions from the ion-source electrode to one of the synthesis locations, by activation of the activating electrode associated with the one of the synthesis locations.

2. The device according to claim 1, wherein the ion-source electrode is an insertion electrode.

3. The device according to claim 2, wherein the ion-source electrode is an ion intercalation electrode.

4. The device according to claim 2, further comprising a plurality of ion-source electrodes, wherein each one of the plurality of the ion-source electrodes is arranged in connection with one of the synthesis locations, respectively.

5. The device according to claim 2, wherein the synthesis locations are arranged to be in contact with reactants, reaction products, and reaction media.

6. The device according to claim 2, wherein the synthesis locations comprise porous oxides configured to support the synthesis of the macromolecules.

7. The device according to claim 1, wherein the ion intercalation electrode is formed of a material comprising amorphous $TiO_2$, amorphous chlorine doped $TiO_2$, nanoporous silica, or nanoporous titania.

8. The device according to claim 1, further comprising a plurality of ion-source electrodes, wherein each one of the plurality of the ion-source electrodes is arranged in connection with one of the synthesis locations, respectively.

9. The device according to claim 1, wherein the synthesis locations are arranged to be in contact with reactants, reaction products, and reaction media.

10. The device according to claim 1, wherein the synthesis locations comprise porous oxides configured to support the synthesis of the macromolecules.

11. The device according to claim 1, further comprising a counter electrode arranged at a distance from the synthesis surface,
    wherein activation of the activating electrodes associated with the synthesis locations is realized by provision of voltage and/or current between the activating electrodes and the counter electrode.

12. The device according to claim 11, further comprising a control unit arranged to control activation of the activating electrodes.

13. The device according to claim 12, wherein the counter electrode and the ion-source electrode are made of the same material.

14. The device according to claim 11, further comprising:
    a synthesis plate having a first side and a second side and an array of through holes, one through hole for each of the synthesis locations, the through holes extending from the first side to the second side of the synthesis plate,
    wherein the first side of the synthesis plate is arranged to be in contact with the synthesis surface of the ion-releaser, each of the through holes being associated with one of the synthesis locations, respectively, the synthesis surface of the ion-releaser forming a bottom portion of each of the through holes, thereby defining a synthesis cavity in each of the through holes comprising a synthesis location.

15. The device according to claim 14, wherein the counter electrode is arranged to be in contact with the second side of the synthesis plate, and wherein the counter electrode comprises openings in connection with each of the synthesis cavities, thereby allowing transport of matter into or out of each of the synthesis cavities.

16. The device according to claim 11, wherein the counter electrode and the ion-source electrode are made of the same material.

17. The device according to claim 1, wherein the releasable ions are ions acting as reactants in the synthesis of the macromolecules, or ions providing catalytic effects on the synthesis of the macromolecules.

18. The device according to claim 1, wherein the releasable ions are selected from protons, $Li^+$, $Na^+$, $Al^{3+}$, $Ca^{2+}$, $Cu^+$ and $Mg^{2+}$, and combinations thereof.

19. A method of synthesis of macromolecules, the method comprising:
   providing reactants for the synthesis on at least one of the synthesis locations of the synthesis device of claim 1;
   releasing at least a portion of the releasable ions from the ion-source electrode to the at least one of the synthesis locations; and
   synthesizing the macromolecules from the reactants in the presence of the released ions, on the at least one of the synthesis locations.

\* \* \* \* \*